(12) United States Patent
Takahashi

(10) Patent No.: US 12,194,172 B2
(45) Date of Patent: Jan. 14, 2025

(54) CONTROL DEVICE, IN-VEHICLE STERILIZATION SYSTEM, CONTROL METHOD, AND CONTROL PROGRAM

(71) Applicant: TOYOTA JIDOSHA KABUSHIKI KAISHA, Toyota (JP)

(72) Inventor: Taro Takahashi, Urayasu (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 449 days.

(21) Appl. No.: 17/592,959

(22) Filed: Feb. 4, 2022

(65) Prior Publication Data
US 2022/0288250 A1    Sep. 15, 2022

(30) Foreign Application Priority Data

Mar. 15, 2021   (JP) ................................ 2021-041596

(51) Int. Cl.
*A61L 2/10* (2006.01)
*B60S 1/64* (2006.01)
*B60H 1/00* (2006.01)

(52) U.S. Cl.
CPC . *A61L 2/10* (2013.01); *B60S 1/64* (2013.01); *A61L 2202/11* (2013.01); *A61L 2202/14* (2013.01); *B60H 1/00828* (2013.01)

(58) Field of Classification Search
CPC .... A61L 2/10; A61L 2202/11; A61L 2202/14; A61L 9/20; A61L 2209/111; B60S 1/64; B60H 1/00828; B60H 3/0078; B60H 1/00742; B60H 3/00
See application file for complete search history.

(56) References Cited

U.S. PATENT DOCUMENTS

| | | | |
|---|---|---|---|
| 2020/0061223 A1* | 2/2020 | Hallack | B60N 2/002 |
| 2022/0055447 A1* | 2/2022 | Van Wiemeersch | B60H 1/00735 |
| 2022/0118822 A1* | 4/2022 | Gutowski | B60H 1/00021 |
| 2022/0125975 A1* | 4/2022 | MacKenzie | B60Q 9/00 |
| 2022/0193278 A1* | 6/2022 | Lee | A61L 2/24 |

FOREIGN PATENT DOCUMENTS

| | | |
|---|---|---|
| CN | 112316165 A | 2/2021 |
| JP | 2010-076529 A | 4/2010 |
| JP | 2012-254673 A | 12/2012 |
| JP | 2019-209827 A | 12/2019 |

\* cited by examiner

*Primary Examiner* — Adam R Mott
*Assistant Examiner* — Sagar Kc
(74) *Attorney, Agent, or Firm* — Oliff PLC

(57) ABSTRACT

A control device that controls an ultraviolet emission device such that the inside of a vehicle is sterilized is provided. The control device includes a vehicle state acquiring unit configured to acquire a state of the vehicle, a determination unit configured to determine whether a person is present inside of the vehicle based on the state of the vehicle, and a control unit configured to control the ultraviolet emission device with reference to a result of determination of whether a person is present inside of the vehicle.

9 Claims, 7 Drawing Sheets

CONTROL DEVICE, IN-VEHICLE STERILIZATION SYSTEM, CONTROL METHOD, AND CONTROL PROGRAM

CROSS-REFERENCE TO RELATED APPLICATION

This application claims priority to Japanese Patent Application No. 2021-041596 filed on Mar. 15, 2021, incorporated herein by reference in its entirety.

BACKGROUND

1. Technical Field

The present disclosure relates to a control device, an in-vehicle sterilization system, a control method, and a control program and more particularly to, for example, a control device, an in-vehicle sterilization system, a control method, and a control program that control an ultraviolet emission device such that the inside of a vehicle can be sterilized.

2. Description of Related Art

For example, an in-vehicle cleanup system disclosed in Japanese Unexamined Patent Application Publication No. 2010-76529 (JP 2010-76529 A) includes a light emission device that is disposed in a space in which food such as vegetables or fruit is accommodated and is configured to irradiate the space with ultraviolet light using the light emission device. Accordingly, it is possible to achieve sterilization effects or deodorization effects. Such an in-vehicle cleanup system is configured to activate the light emission device when an ignition switch is turned on.

SUMMARY

The applicant of the present disclosure found the following problems. The in-vehicle cleanup system described in JP 2010-76529 A is configured to necessarily activate the light emission device when the ignition switch is turned on, that is, when a user uses a vehicle, and there is a likelihood that some users will feel discomfort from unexpected emission of ultraviolet light.

The present disclosure provides a control device, an in-vehicle sterilization system, a control method, and a control program that can sterilize the inside of a vehicle while curbing a user's discomfort.

According to an aspect of the present disclosure, there is provided a control device that controls an ultraviolet emission device such that the inside of a vehicle is sterilized, the control device including: a vehicle state acquiring unit configured to acquire a state of the vehicle; a determination unit configured to determine whether a person is present inside of the vehicle based on the state of the vehicle; and a control unit configured to control the ultraviolet emission device with reference to a result of determination of whether a person is present inside of the vehicle.

In the control device, the vehicle state acquiring unit may be configured to acquire a schedule of use of the vehicle, and the determination unit may be configured to determine whether a person is present inside of the vehicle based on the schedule of use of the vehicle.

The control device may further include a plan establishing unit configured to establish a plan for sterilizing the inside of the vehicle using the ultraviolet emission device based on the schedule of use of the vehicle.

In the control device, the vehicle state acquiring unit may be configured to acquire a state of use of the vehicle, and the determination unit may be configured to determine whether a person is present inside of the vehicle based on the state of use of the vehicle.

According to an aspect of the present disclosure, there is provided an in-vehicle sterilization system including the control device and the ultraviolet emission device.

In the in-vehicle sterilization system, the ultraviolet emission device may be provided in the vehicle such that a place in contact with a person inside of the vehicle is able to be irradiated with ultraviolet light.

The in-vehicle sterilization system may further include a first detection device that detects a state of use of the vehicle.

The in-vehicle sterilization system may further include a second detection device that detects a residual capacity or a voltage of a battery of the vehicle, and a control unit of the ultraviolet emission device may be configured to stop emission of ultraviolet light from the ultraviolet emission device when the residual capacity or the voltage of the battery of the vehicle is less than a preset threshold value.

The in-vehicle sterilization system may further include an operation unit for the control device that is used to operate the ultraviolet emission device according to a person from the outside.

The in-vehicle sterilization system may further include a ventilator that ventilates the inside of the vehicle.

According to an aspect of the present disclosure, there is provided a control method of controlling an ultraviolet emission device such that the inside of a vehicle is sterilized, the control method including: acquiring a state of the vehicle; determining whether a person is present inside of the vehicle based on the state of the vehicle; and controlling the ultraviolet emission device with reference to a result of determination of whether a person is present inside of the vehicle.

According to an aspect of the present disclosure, there is provided a control program for controlling an ultraviolet emission device such that the inside of a vehicle is sterilized, the control program causing a computer to perform: acquiring a state of the vehicle; determining whether a person is present inside of the vehicle based on the state of the vehicle; and controlling the ultraviolet emission device with reference to a result of determination of whether a person is present inside of the vehicle.

According to the present disclosure, it is possible to provide a control device, an in-vehicle sterilization system, a control method, and a control program that can sterilize the inside of a vehicle while curbing a user's discomfort.

BRIEF DESCRIPTION OF THE DRAWINGS

Features, advantages, and technical and industrial significance of exemplary embodiments of the disclosure will be described below with reference to the accompanying drawings, in which like signs denote like elements, and wherein.

DETAILED DESCRIPTION OF EMBODIMENTS

Hereinafter, exemplary embodiments of the present disclosure will be described in detail with reference to the accompanying drawings. The present disclosure is not limited to the following embodiments. For the purpose of facilitation of description, the following description and the drawings are appropriately simplified.

First Embodiment

Figure 1:
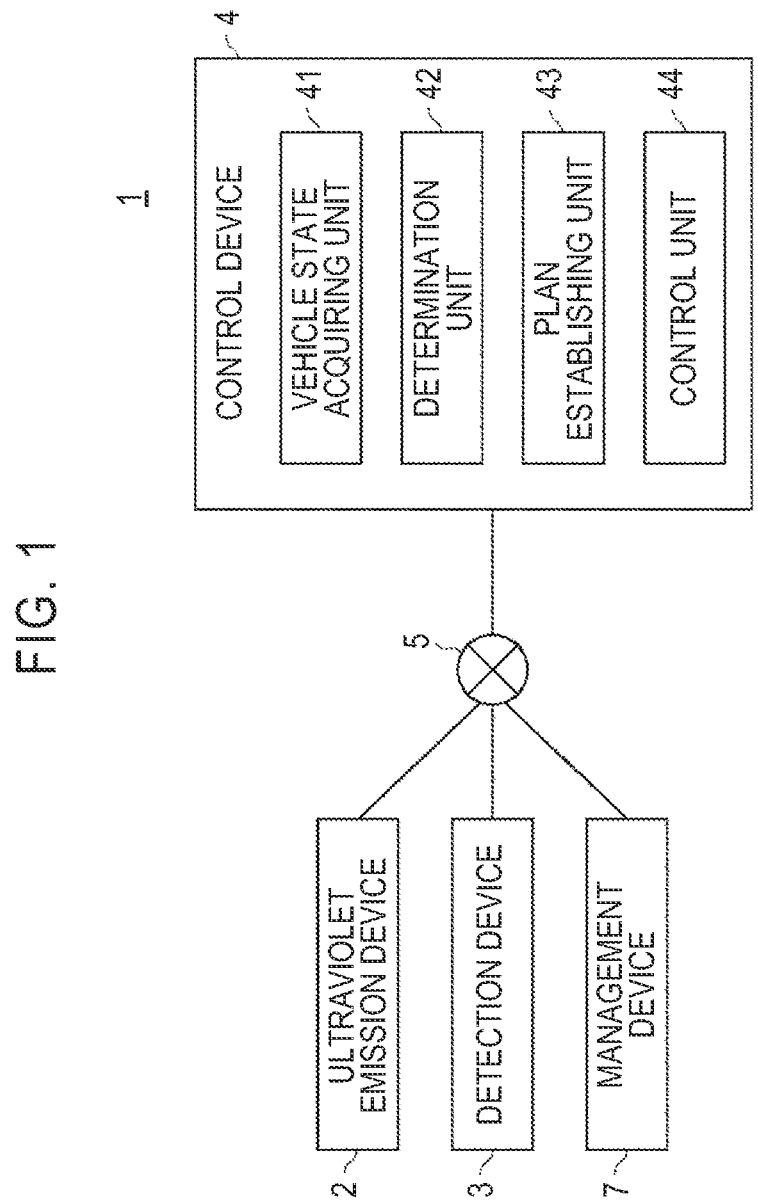
FIG. 1 is a block diagram illustrating a control system of an in-vehicle sterilization system according to a first embodiment.

An in-vehicle sterilization system according to a first embodiment can be suitably used to sterilize the inside of a vehicle which is used, for example, for car-sharing. FIG. 1 is a block diagram illustrating a control system of the in-vehicle sterilization system according to this embodiment. In the present disclosure, "sterilization" is not limited to disinfection or sterilization has and includes a concept including deactivation of viruses.

As illustrated in FIG. 1, an in-vehicle sterilization system 1 includes an ultraviolet emission device 2, a detection device 3, and a control device 4, which are connected to each other via a network 5. Here, the network 5 is, for example, the Internet which is constructed by a telephone circuit network, a radio communication line, Ethernet (registered trademark), and the like. The ultraviolet emission device 2, the detection device 3, and the control device 4 can be connected to each other in a wired or wireless manner.

Figure 2:
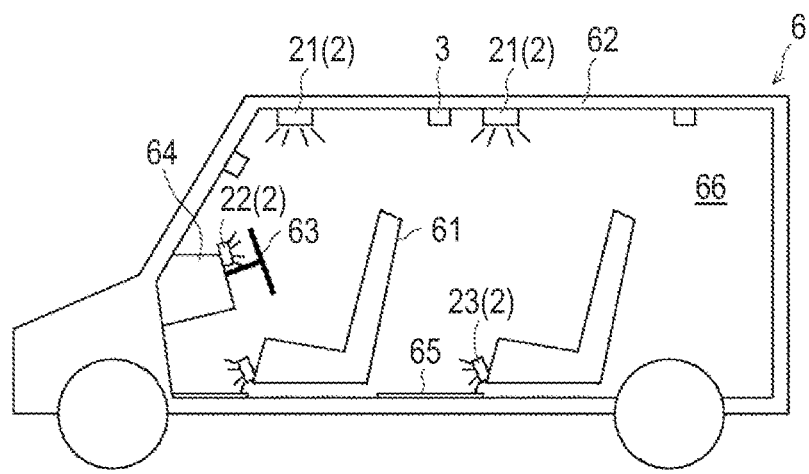
FIG. 2 is a diagram illustrating arrangement of an ultraviolet emission device and a detection device according to the first embodiment.

The ultraviolet emission device 2 emits, for example, ultraviolet light in a wavelength range of about 10 nm to 400 nm. FIG. 2 is a diagram illustrating arrangement of the ultraviolet emission device and the detection device according to this embodiment. As illustrated in FIG. 2, the ultraviolet emission device 2 is arranged inside of a vehicle 6. At this time, the ultraviolet emission device 2 can be arranged inside of the vehicle 6 such that a place in contact with a person inside of the vehicle 6 is able to be irradiated with ultraviolet light.

Specifically, in this embodiment, the ultraviolet emission device 2 includes a first ultraviolet emission device 21, a second ultraviolet emission device 22, and a third ultraviolet emission device 23. The first ultraviolet emission device 21 is provided inside of the vehicle 6 such that a seat 61, an armrest, or the like of the vehicle 6 is able to be irradiated with ultraviolet light and is provided, for example, on a ceiling 62 of the vehicle 6.

The second ultraviolet emission device 22 is provided inside of the vehicle 6 such that the rear of a steering wheel 63 of the vehicle 6 is irradiated with ultraviolet light and is provided, for example, on a front panel 64 of the vehicle 6. The third ultraviolet emission device 23 is provided inside of the vehicle 6 such that a floor mat 65 of the vehicle 6 is able to be irradiated with ultraviolet light and is provided, for example, below the seat 61 of the vehicle 6. Here, the arrangement or the number of the ultraviolet emission device 2 is not particularly limited as long as it can irradiate a place in contact with a person inside of the vehicle 6 with ultraviolet light.

The detection device 3 detects a state of use of the vehicle 6 such as a person having boarded or alighted from the vehicle 6. The detection device 3 includes, for example, a camera. As illustrated in FIG. 2, the detection device 3 is provided inside of the vehicle 6 such that the seat 61, a bucket space 66, or the like of the vehicle 6 is included in an imaging range and is provided, for example, on the ceiling 62 of the vehicle 6.

The detection device 3 has only to have a configuration or arrangement that can detect a person present inside of the vehicle 6, and may include a weight sensor or a respiration sensor provided in the seat 61 of the vehicle 6, an infrared camera, or the like.

The control device 4 includes a vehicle state acquiring unit 41, a determination unit 42, a plan establishing unit 43, and a control unit 44. The vehicle state acquiring unit 41 acquires a state of the vehicle 6. The vehicle state acquiring unit 41 acquires, for example, a schedule of use of the vehicle 6 or a state of use of the vehicle 6 as the state of the vehicle 6 from a management device 7.

For example, the management device 7 is owned by a car-sharing company to manage the schedule of use of the vehicle 6 or the like and is connected to the network 5. The management device 7 generates a schedule of use, for example, based on a desired use time period of the vehicle 6 which has been input by a person who wants to use the vehicle 6 (that is, a user).

For example, the vehicle state acquiring unit 41 acquires an image obtained by imaging the inside of the vehicle 6 as the state of the vehicle 6 from the detection device 3. The vehicle state acquiring unit 41 has only to be able to acquire the state of the vehicle 6 and, for example, may acquire a desired use time period of the vehicle 6 input by a user without using the management device 7 or may include the detection device 3.

The determination unit 42 determines whether a person including a user is present inside of the vehicle 6 based on the state of the vehicle 6. That is, for example, the determination unit 42 may determine that a person is not present inside of the vehicle 6 in a time period in which a schedule of use of the vehicle 6 has a vacancy and determines that a person is present inside of the vehicle 6 in other time periods.

Here, when the use of the vehicle 6 ends earlier than that in the schedule of use based on the state of use of the vehicle 6, the determination unit 42 can determine that a person is not present inside of the vehicle 6.

Based on an image obtained by imaging the inside of the vehicle 6, the determination unit 42 determines whether a person is present inside of the vehicle 6 and determines whether a person has boarded or alighted from the vehicle 6. For example, when it is determined that a person has boarded the vehicle 6 based on the image, the determination unit 42 may determine that a user has started the use of the vehicle 6 and a person is present inside of the vehicle 6. On the other hand, for example, when it is determined that a person has alighted from the vehicle 6 based on the image, the determination unit 42 may determine that the user has ended the use of the vehicle 6 and a person is not present inside of the vehicle 6.

The plan establishing unit 43 establishes a plan to sterilize the inside of the vehicle 6 using the ultraviolet emission device 2. For example, the plan establishing unit 43 establishes a plan to sterilize the inside of the vehicle 6 using the ultraviolet emission device 2 after a preset first time has elapsed from a use end time of the vehicle 6 and until a preset second time before a use start time of the vehicle 6 in the schedule of use. Here, the plan establishing unit 43 can establish a plan to sterilize the inside of the vehicle 6 using the ultraviolet emission device 2 while a person is not present inside of the vehicle 6.

The control unit 44 controls the ultraviolet emission device 2 with reference to a result of determination of whether a person is present inside of the vehicle 6. For example, the control unit 44 controls the ultraviolet emission device 2 based on the plan to sterilize the inside of the vehicle 6 using the ultraviolet emission device 2.

Figure 3:
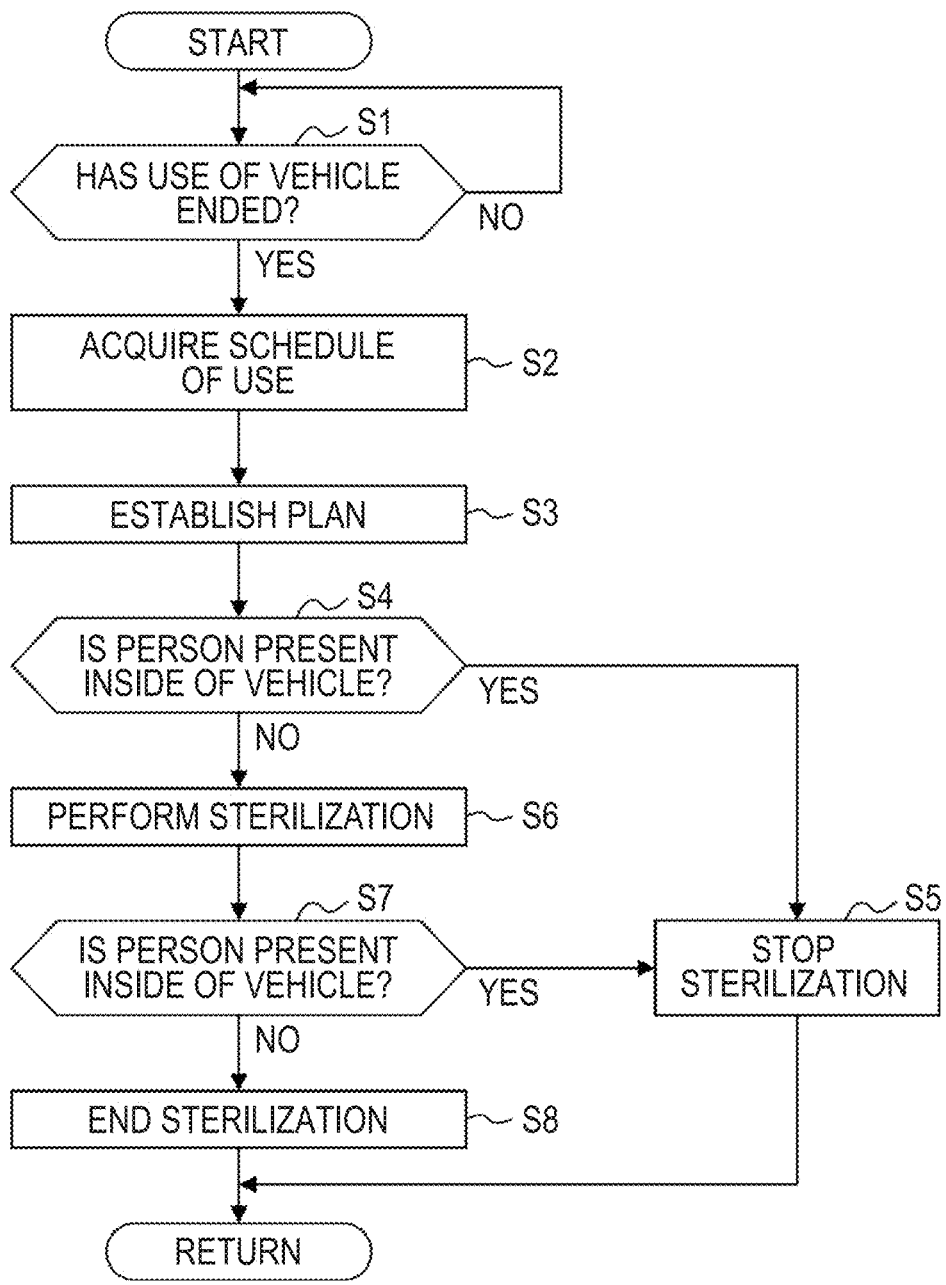
FIG. 3 is a flowchart illustrating a process flow of sterilizing the inside of a vehicle using the in-vehicle sterilization system according to the first embodiment.

A process flow of sterilizing the inside of the vehicle 6 using the in-vehicle sterilization system 1 according to this embodiment will be described below. FIG. 3 is a flowchart illustrating a process flow of sterilizing the inside of a vehicle using the in-vehicle sterilization system according to this embodiment. Here, it is assumed that the vehicle state acquiring unit 41 of the control device 4 acquires an image of the inside of the vehicle 6 from the detection device 3 in real time.

First, the determination unit 42 of the control device 4 determines whether a user has alighted from the vehicle 6 and ended use of the vehicle 6 based on an image of the inside of the vehicle 6 (S1). When it is determined that the user has not ended use of the vehicle 6 (NO in S1), the determination unit 42 of the control device 4 returns to the process of S1.

On the other hand, when it is determined that the user has alighted from the vehicle 6 and ended use of the vehicle 6 (YES in S1), the vehicle state acquiring unit 41 of the control device 4 acquires a schedule of use of the vehicle 6 from the management device 7 (S2).

Then, the plan establishing unit 43 of the control device 4 establishes a plan to sterilize the inside of the vehicle 6 using the ultraviolet emission device 2, that is, to irradiate the inside of the vehicle 6 using the ultraviolet emission device 2 based on a schedule of use of the vehicle 6 (S3). Then, when it is time to start irradiation with ultraviolet light using the ultraviolet emission device 2, the determination unit 42 of the control device 4 determines whether a person including the user is present inside of the vehicle 6 based on an image of the inside of the vehicle 6 (S4).

When a person is present inside of the vehicle 6 (YES in S4), the control device 4 stops sterilization of the inside of the vehicle 6 using the ultraviolet emission device 2 (S5). On the other hand, when a person is not present inside of the vehicle 6 (NO in S4), the control unit 44 of the control device 4 controls the ultraviolet emission device 2 such that sterilization of the inside of the vehicle 6 using the ultraviolet emission device 2 is performed (S6).

At this time, the determination unit 42 of the control device 4 determines whether a person is present inside of the vehicle 6 based on an image of the inside of the vehicle 6 (S7), and the control unit 44 can control the ultraviolet emission device 2 such that sterilization of the inside of the vehicle 6 using the ultraviolet emission device 2 is stopped (S5) when a person is present inside of the vehicle 6 (YES in S7). On the other hand, when a person is not present inside of the vehicle 6 (NO in S7), the control unit 44 continues to sterilize the inside of the vehicle 6 using the ultraviolet emission device 2.

Then, when it is time to end the irradiation with ultraviolet light using the ultraviolet emission device 2, the control unit 44 of the control device 4 controls the ultraviolet emission device 2 such that sterilization of the inside of the vehicle 6 using the ultraviolet emission device 2 ends (S8).

With the in-vehicle sterilization system 1, the control device 4, and the control method according to this embodiment, it is ascertained that a person including the user is not present inside of the vehicle 6 based on the state of the vehicle 6 and sterilization of the inside of the vehicle 6 using the ultraviolet emission device 2 is performed while a person is not present inside of the vehicle 6. Accordingly, sterilization of the inside of the vehicle 6 using the ultraviolet emission device 2 is not performed at a timing which is not intended by a user and thus it is possible to curb the user's discomfort.

When the vehicle 6 is a vehicle for car-sharing, use time periods of the vehicle 6 of a plurality of users can be acquired together from the management device 7 based on the schedule of use of the vehicle 6 and a plan to sterilize the inside of the vehicle 6 using the ultraviolet emission device 2 can be simply established.

Since the state of use of the vehicle 6 is detected by the detection device 3, it is possible to perform sterilization of the inside of the vehicle 6 using the ultraviolet emission device 2 while ascertaining that a person is not present inside of the vehicle 6. Accordingly, for example, when a user returns to the vehicle 6 to take a lost object, it is possible to reliably stop sterilization of the inside of the vehicle 6 using the ultraviolet emission device 2.

Second Embodiment

Figure 4:
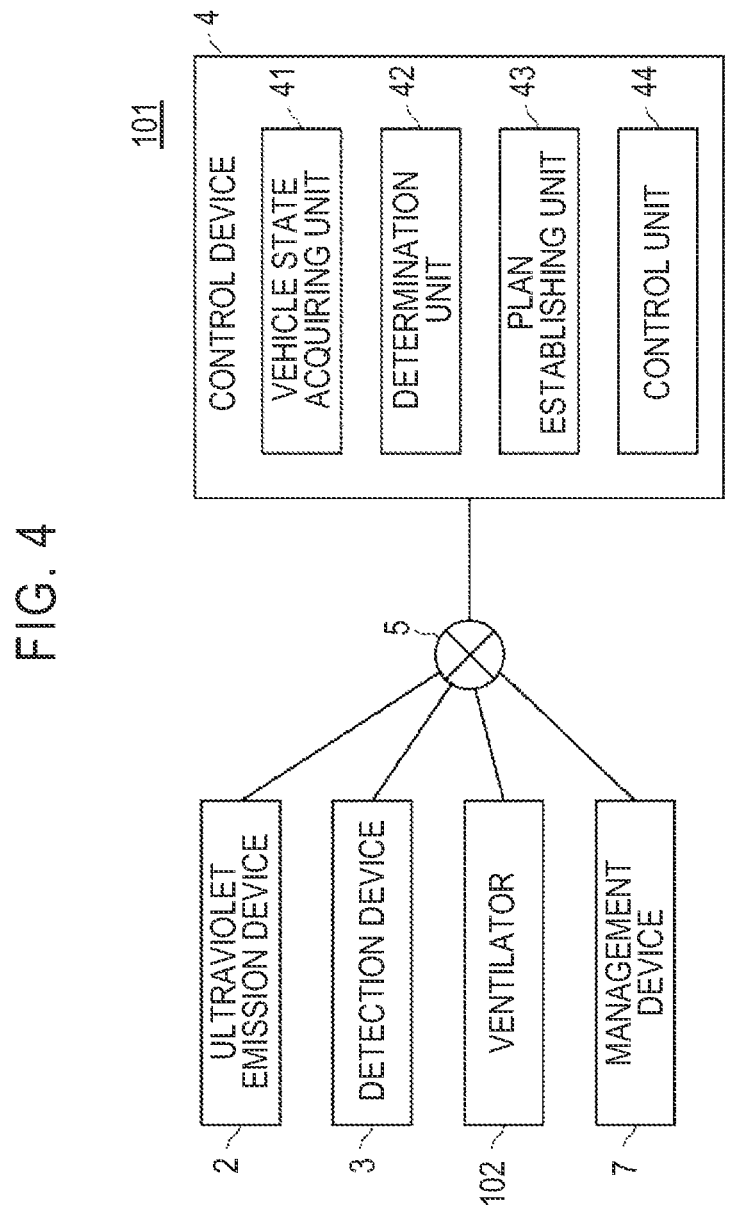
FIG. 4 is a block diagram illustrating a control system of an in-vehicle sterilization system according to a second embodiment.

FIG. 4 is a block diagram illustrating a control system of an in-vehicle sterilization system according to a second embodiment. Since an in-vehicle sterilization system 101 according to this embodiment has substantially the same configuration as the in-vehicle sterilization system 1 according to the first embodiment, description thereof will be omitted, and the same elements will be referred to by the same reference signs.

The in-vehicle sterilization system 101 according to this embodiment is different from the in-vehicle sterilization system 1 according to the first embodiment in that a ventilator 102 is further provided. The ventilator 102 is configured to ventilate the inside of the vehicle 6 and is provided in the vehicle 6. For example, the ventilator 102 can operate while sterilization of the inside of the vehicle 6 using the ultraviolet emission device 2 is being performed. Accordingly, it is possible to improve sterilization effects of the inside of the vehicle 6.

Third Embodiment

Figure 5:
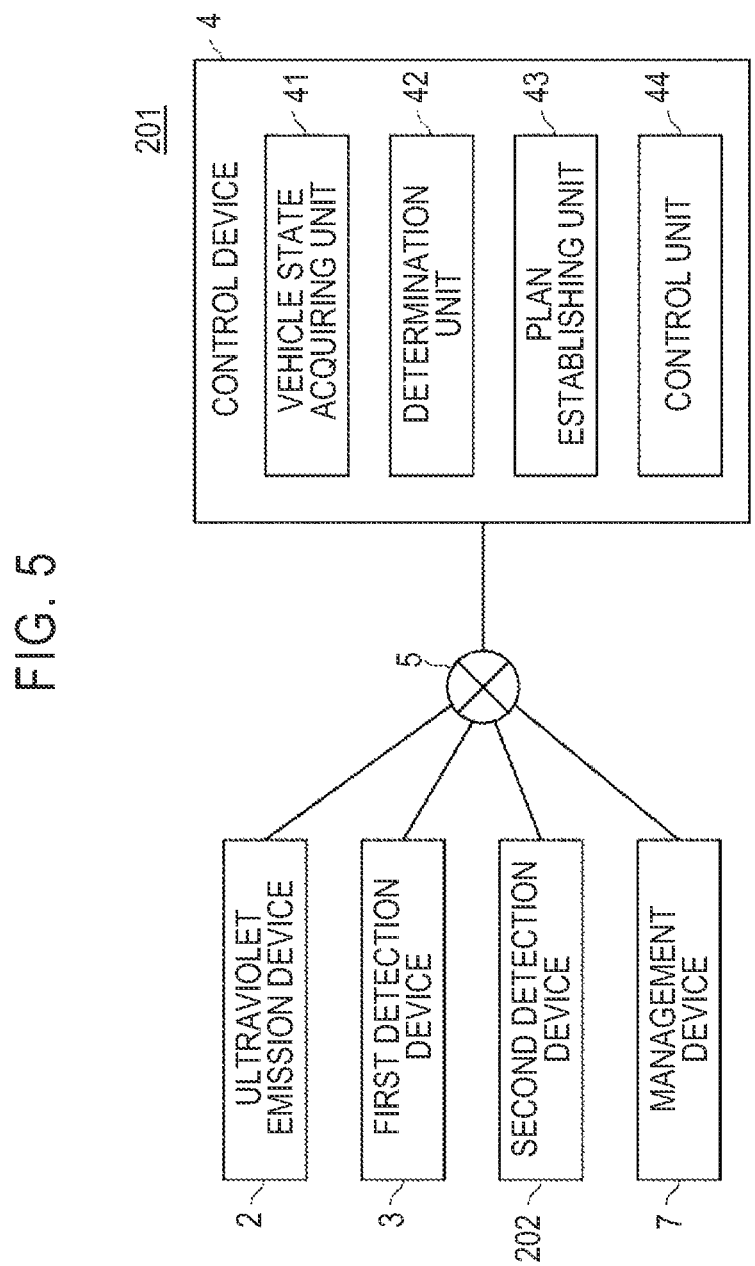
FIG. 5 is a block diagram illustrating a control system of an in-vehicle sterilization system according to a third embodiment.

FIG. 5 is a block diagram illustrating a control system of an in-vehicle sterilization system according to a third embodiment. Since an in-vehicle sterilization system 201 according to this embodiment has substantially the same configuration as the in-vehicle sterilization system 1 according to the first embodiment, description thereof will be omitted, and the same elements will be referred to by the same reference signs.

The in-vehicle sterilization system 201 according to this embodiment is different from the in-vehicle sterilization system 1 according to the first embodiment, in that a second detection device 202 that detects a residual capacity or a voltage of a battery of the vehicle 6 is provided in addition to the detection device (first detection device) 3.

Accordingly, for example, when the residual capacity or the voltage of the battery of the vehicle 6 is less than a preset threshold value, the control unit 44 of the control device 4 can stop sterilization of the inside of the vehicle 6 using the ultraviolet emission device 2 and curb over-discharging of the battery of the vehicle 6.

Fourth Embodiment

Figure 6:
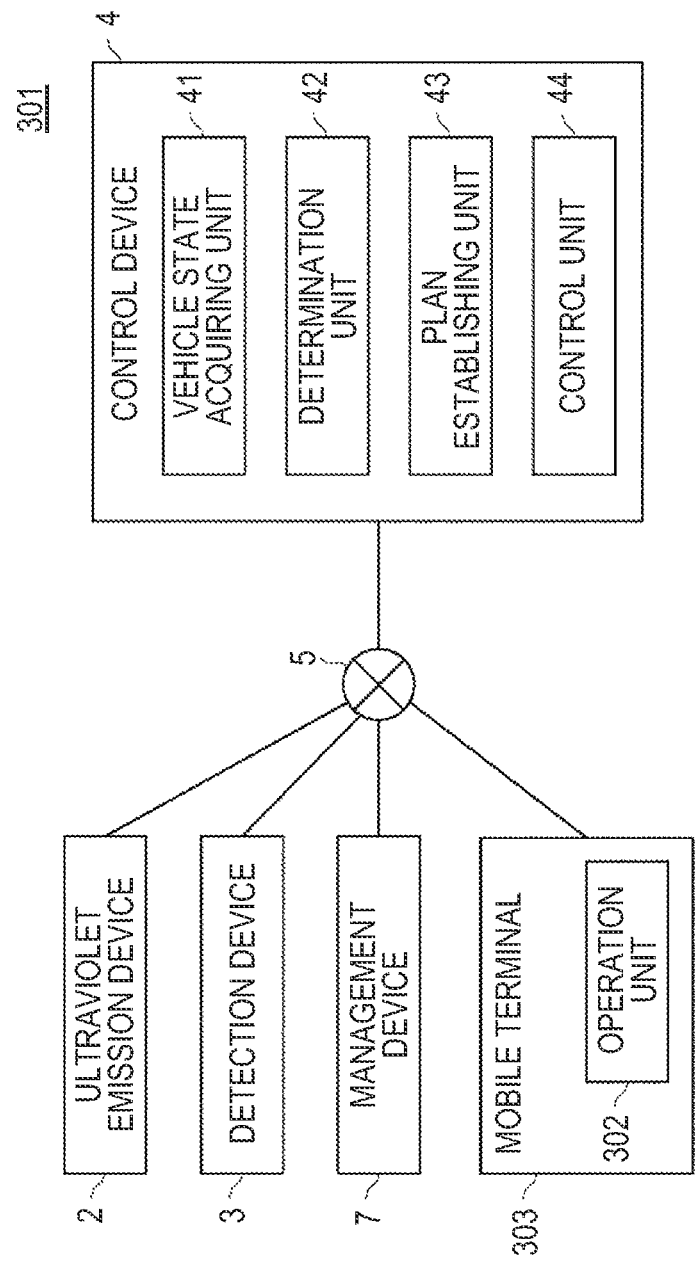
FIG. 6 is a block diagram illustrating a control system of an in-vehicle sterilization system according to a fourth embodiment.

FIG. 6 is a block diagram illustrating a control system of an in-vehicle sterilization system according to a fourth embodiment. Since an in-vehicle sterilization system 301 according to this embodiment has substantially the same configuration as the in-vehicle sterilization system 1 according to the first embodiment, description thereof will be omitted, and the same elements will be referred to by the same reference signs.

The in-vehicle sterilization system 301 according to this embodiment is different from the in-vehicle sterilization system 1 according to the first embodiment, in that an operation unit 302 that is used for a person to operate the ultraviolet emission device 2 from the outside is further provided. The operation unit 302 is mounted, for example, in a mobile terminal 303 carried by a user of the vehicle 6 and is connected to the network 5.

By allowing a user to operate the operation unit 302, the operation unit 302 turns on/off the ultraviolet emission device 2 or transmits operation information for designating a time period in which the ultraviolet emission device 2 is to operate to the control device 4.

Even when it is determined that a person is present inside of the vehicle 6, the control unit 44 of the control device 4 can give priority to the operation information of the operation unit 302 and control the ultraviolet emission device 2 such that sterilization of the inside of the vehicle 6 using the ultraviolet emission device 2 is performed.

In this case, for example, since a user is present inside of the vehicle 6 but the user recognizes that sterilization of the inside of the vehicle 6 using the ultraviolet emission device 2 is being performed and the irradiation with ultraviolet light is not unexpected, it is possible to curb the user's discomfort.

In this embodiment, priority is given to the operation information of the operation unit 302, but, for example, priority may be given to a detection result from the detection device 3 and sterilization of the inside of the vehicle 6 using the ultraviolet emission device 2 may be stopped when a person is present inside of the vehicle 6.

OTHER EMBODIMENTS

Figure 7:
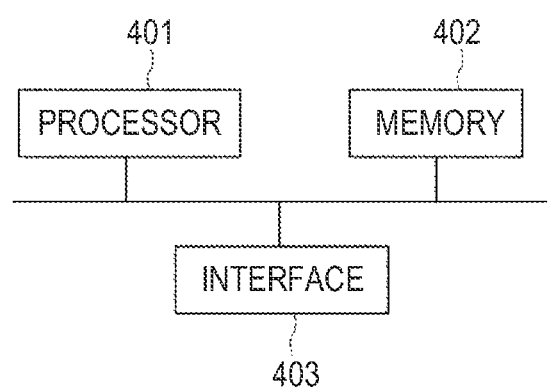
FIG. 7 is a diagram illustrating an example of a hardware configuration of an in-vehicle sterilization system and a control device.

The in-vehicle sterilization systems and the control devices according to the aforementioned embodiments may have the following hardware configuration. FIG. 7 is a diagram illustrating a hardware configuration included in the in-vehicle sterilization systems and the control devices. As in the process flow in the in-vehicle sterilization system and the control device as described in the aforementioned embodiments, the present disclosure can be realized as a control method.

The device illustrated in FIG. 7 includes an interface 403, a processor 401, and a memory 402. Some constituents of the in-vehicle sterilization systems and the control devices described in the aforementioned embodiments can be realized by causing the processor 401 to read and execute a program stored in the memory 402. That is, the program is a program for causing the processor 401 to serve as some constituents of the in-vehicle sterilization system and the control device. The program can be said to be a program for causing the in-vehicle sterilization system and the control device to realize their configurations or to perform processes in some thereof.

The aforementioned program can be stored in various types of non-transitory computer-readable media and supplied to a computer (a computer including an information transmitting device). The non-transitory computer-readable media include various types of tangible storage media. Examples of the non-transitory computer-readable storage media include a magnetic storage medium (for example, a flexible disk, a magnetic tape, or a hard disk drive) and a magneto-optical storage medium (for example, a magneto-optical disc). The examples include a compact disc read only memory (CD-ROM), a CD-R, and a CD-R/W. The examples include a semiconductor memory (for example, a mask ROM, a PROM, an EPROM, a flash ROM, or a RAM). The program may be supplied to a computer using various types of transitory computer-readable media. Examples of the transitory computer-readable media include an electrical signal, an optical signal, and electromagnetic waves. The transitory computer-readable media can supply a program to a computer via a wired communication line such as an electrical wire or an optical fiber or a wireless communication line.

The present disclosure is not limited to the aforementioned embodiments and can be appropriately modified without departing from the gist thereof.

For example, a plurality of the embodiments may be implemented in a combined manner.

For example, in the aforementioned embodiments, a person present inside of the vehicle 6 is detected, but an animal such as a pet may be detected and the ultraviolet emission device 2 may be controlled with reference to a result of determination of whether a person or a pet is present inside of the vehicle 6.

For example, in the aforementioned embodiments, a plan to sterilize the inside of the vehicle 6 using the ultraviolet emission device 2 is established based on the schedule of use of the vehicle 6, but emission of ultraviolet light from the ultraviolet emission device 2 may be performed while a person is not present inside of the vehicle 6 based on a result of detection from the detection device 3 without acquiring the schedule of use of the vehicle 6. This embodiment is suitable for a vehicle which is owned by a user and the plan establishing unit 43 may be omitted.

For example, in the aforementioned embodiments, the result of detection from the detection device 3 is referred to, but the detection device 3 may be omitted and emission of ultraviolet light from the ultraviolet emission device 2 may be performed based on the schedule of use of the vehicle 6.

For example, when the schedule of use of the vehicle 6 is used, the determination unit 42 of the control device 4 does not need to directly determine whether a person is present inside of the vehicle 6, but can indirectly determine whether a person is present inside of the vehicle 6 when time periods in which the vehicle 6 is not being used are extracted. That is, "determine whether a person is present inside of the vehicle 6" is a concept including a case of direct determination thereof in addition to a case of indirect determination thereof.

What is claimed is:

1. A control device that controls an ultraviolet emission device such that the inside of a vehicle is sterilized, the control device comprising:
   a processor programmed to:
      acquire a schedule of use of the vehicle;

determine whether a person is present inside of the vehicle based on the schedule of use of the vehicle;

establish a plan for sterilizing the inside of the vehicle using the ultraviolet emission device based on the schedule of use of the vehicle; and control the ultraviolet emission device with reference to a result of determination of whether the person is present inside of the vehicle, wherein when the result of the determination is that the person is present inside the vehicle, priority is given to operation information of a mobile terminal that is used to operate the ultraviolet emission device according to the person, such that the ultraviolet emission device is controlled to perform sterilization.

2. An in-vehicle sterilization system comprising:
the control device according to claim 1; and
the ultraviolet emission device.

3. The in-vehicle sterilization system according to claim 2, wherein
the ultraviolet emission device is provided in the vehicle such that a place in contact with the person inside of the vehicle is able to be irradiated with ultraviolet light.

4. The in-vehicle sterilization system according to claim 2, further comprising
a first sensor that detects a state of use of the vehicle.

5. The in-vehicle sterilization system according to claim 2, wherein
the processor is further programmed to stop emission of ultraviolet light from the ultraviolet emission device when a residual capacity or a voltage of a battery of the vehicle is less than a preset threshold value.

6. The in-vehicle sterilization system according to claim 2, further comprising
the mobile terminal that is used to operate the ultraviolet emission device according to the person.

7. The in-vehicle sterilization system according to claim 2, further comprising
a ventilator that ventilates the inside of the vehicle.

8. A control method of controlling an ultraviolet emission device such that the inside of a vehicle is sterilized, the control method comprising:
acquiring a schedule of use of the vehicle;
determining whether a person is present inside of the vehicle based on the schedule of use of the vehicle;
establishing a plan for sterilizing the inside of the vehicle using the ultraviolet emission device based on the schedule of use of the vehicle; and
controlling the ultraviolet emission device with reference to a result of determination of whether the person is present inside of the vehicle, wherein
when the result of the determination is that the person is present inside the vehicle, priority is given to operation information of a mobile terminal that is used to operate the ultraviolet emission device according to the person, such that the ultraviolet emission device is controlled to perform sterilization.

9. A non-transitory computer-readable medium storing thereon a control program for controlling an ultraviolet emission device such that the inside of a vehicle is sterilized, the control program causing a computer to perform:
acquiring a schedule of use of the vehicle;
determining whether a person is present inside of the vehicle based on the schedule of use of the vehicle;
establishing a plan for sterilizing the inside of the vehicle using the ultraviolet emission device based on the schedule of use of the vehicle; and
controlling the ultraviolet emission device with reference to a result of determination of whether the person is present inside of the vehicle, wherein
when the result of the determination is that the person is present inside the vehicle, priority is given to operation information of a mobile terminal that is used to operate the ultraviolet emission device according to the person, such that the ultraviolet emission device is controlled to perform sterilization.

\* \* \* \* \*